US011723958B2

(12) United States Patent
Moser et al.

(10) Patent No.: US 11,723,958 B2
(45) Date of Patent: Aug. 15, 2023

(54) MICROPARTICLE-BASED ENZYME SYSTEMS FOR SELECTIVE REMOVAL OF TARGET MOLECULES

(71) Applicant: SynLife, Inc., Cambridge, MA (US)

(72) Inventors: Felix Moser, Cambridge, MA (US); David Benjamin, Cambridge, MA (US)

(73) Assignee: SYNLIFE, INC., Cambridge, MA (US)

( * ) Notice: Subject to any disclaimer, the term of this patent is extended or adjusted under 35 U.S.C. 154(b) by 0 days.

(21) Appl. No.: 16/854,653

(22) Filed: Apr. 21, 2020

(65) Prior Publication Data

US 2021/0213107 A1  Jul. 15, 2021

Related U.S. Application Data

(60) Provisional application No. 62/958,935, filed on Jan. 9, 2020.

(51) Int. Cl.
*A61K 38/44* (2006.01)
*A61P 39/00* (2006.01)
*A61K 9/127* (2006.01)

(52) U.S. Cl.
CPC .............. *A61K 38/44* (2013.01); *A61K 9/127* (2013.01); *A61P 39/00* (2018.01); *C12Y 106/03001* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,450,153 A | * | 5/1984 | Hopkins | A61K 38/443 424/94.4 |
| 5,759,539 A | * | 6/1998 | Whitmire | A61K 35/74 424/94.2 |
| 2005/0064570 A1 | * | 3/2005 | Hummel | C12N 9/0036 435/191 |
| 2005/0271739 A1 | * | 12/2005 | Wang | A61K 2300/00 424/562 |
| 2010/0130573 A1 | | 5/2010 | Tokunaga | |
| 2014/0050702 A1 | | 2/2014 | Smith et al. | |

(Continued)

OTHER PUBLICATIONS

Chang, "Therapeutic Applications of Polymeric Artificial Cells", Nature Reviews Drug Discovery, Mar. 2005, 4:221-245.

(Continued)

*Primary Examiner* — Gollamudi S Kishore
(74) *Attorney, Agent, or Firm* — Mark S. Cohen; Pearl Cohen Zedek Latzer Baratz LLP (57) ABSTRACT

The present disclosure provides compositions of microparticles and uses thereof for removing toxic or undesirable molecules from an environment, e.g. the blood of a subject. The microparticles can be liposomes. In one embodiment, the aqueous phase of the liposomes contains (i) a system of generating $NAD^+$ from NADH, and (ii) one or more enzymes that are involved in one or more $NAD^+$-dependent reactions that remove the toxic or undesirable molecules from the environment. In one embodiment, the liposomes contain NADH oxidase, alcohol dehydrogenase (ADH) and acetaldehyde dehydrogenase (ALDH) to remove ethanol from the blood of a subject.

9 Claims, 5 Drawing Sheets

(56) References Cited

U.S. PATENT DOCUMENTS

2015/0342923 A1   12/2015   Powell

OTHER PUBLICATIONS

Bulbake et al., "Liposomal Formulations in Clinical Use: An Updated Review", Pharmaceutics 2017, 9, 12, 33 pages.
Webb et al., "Using microfluids for scalable manufacturing of nanomedicines from bench to GMP: A case study using protein-loaded liposomes", International Journal of Pharmaceutics, 2020, https://doi.org/10.1016/j.ijpharm.2020.119266.
International Search Report and Written Opinion, dated Apr. 2, 2021, from corresponding International Application No. PCT/US21/12599.
Faut et al., "Metabolism of ethanol to acetaldehyde and increased susceptibility to oxidative stress could play a role in the ovarian tissue cell injury promoted by alcohol drinking", Toxicology and Industrial Health, 2009, 25(8):525-538.
Maherani et al., "Liposomes: A Review of Manufacturing Techniques and Targeting Strategies", Current Nanoscience, 2011, 7(3):436-452.
Pratsinis et al., "Liposome-supported enzymatic peritoneal dialysis", Biomaterials 145 (2017) 128-137.
Colletier et al., "Protein encapsulation in liposomes: efficiency depends on interactions between protein and phospholipid bilayer", BMC Technology 2002, 2:9; May 10, 2002, 8 pages.
Hwang et al., "Effects of operating parameters on the efficiency of liposomal encapsulation of enzymes", Colloids and Surfaces B: Biointerfaces 94 (2012) 296-303.

\* cited by examiner

MICROPARTICLE-BASED ENZYME SYSTEMS FOR SELECTIVE REMOVAL OF TARGET MOLECULES

CROSS-REFERENCE TO RELATED APPLICATION

This application claims priority under 35 U.S.C. § 119 (e) to U.S. provisional patent application Ser. No. 62/958,935, filed Jan. 9, 2020, which is incorporated herein by reference in its entirety.

BACKGROUND

When the concentration of a given chemical compound rises above a threshold level in the body, it generates toxicity. For most compounds, this level is quite high and can be easily corrected by the body's homeostatic mechanisms, such as through elimination by chemical catabolism in the liver or by physical filtering via the kidneys. If the body lacks the metabolic or physical machinery to break down a compound, it cannot be eliminated and eventually reaches concentrations where it becomes toxic, leading to illness or death. For patients that consume excess amounts of a compound (e.g. in cases of accidental poisoning, drug use, binge drinking, or overdosing) or for patients that lack critical catabolic enzymes or tissues, there is often little physicians can do to save them. While administration of absorptive agents (e.g. charcoal) or emetics can slow uptake of a compound, few options exist to speed elimination from the blood. While dialysis is an option for some poisoning indications (e.g. salicylic acid, lithium, isopropanol, magnesium-containing laxatives, or ethylene glycol), it is ineffective for many other compounds. Dialysis is also slow to administer and carries the risks of sepsis, low blood pressure, muscle cramps, and pruritus. What is needed in many cases is a means of selectively eliminating specific molecules from the blood without causing further burden to the patient's physiology.

Alcohol poisoning kills approximately 2200 Americans annually. Acute alcohol-related visits to emergency departments numbered over 2.4 million in 2014, with many patients staying an average of 6 hours under intense supervision, resulting in costs of medical care exceeding $15 billion annually. The median blood-alcohol concentration (BAC) of patients who die of alcohol poisoning is 0.36 g/dL. For patients with a BAC that is this high, neither activated charcoal, saline, or fructose injections have been shown to be effective at preventing death. Metadoxine initially showed promise in increasing the natural rate of ethanol elimination but has yet to be approved for the ethanol poisoning indication by the US FDA.

Once consumed, ethanol is rapidly absorbed after entering the small intestines. The majority (>95%) of ethanol is metabolized by human alcohol dehydrogenase (ADH) in conjunction with acetaldehyde dehydrogenase (ALDH) in the liver. ADH oxides ethanol to acetaldehyde and uses the cofactor nicotinamide adenine dinucleotide ($NAD^+$) as an electron acceptor. ALDH, in turn, oxidizes acetaldehyde to acetate and also uses $NAD^+$ as an electron acceptor. Due to the importance of $NAD^+$ as a cofactor in both reactions, ADH and ALDH are primarily found in the $NAD^+$-rich cytoplasm and mitochondrial lumen of hepatocytes. Minor (<5%) contributions to ethanol elimination are made by the stomach tissue and gut microbiota. For patients with highly active ADH or relatively inactive ALDH genetic variants, the accumulation of the acetaldehyde intermediate can result in "alcohol flush," which is characterized by reddening of the skin, heart palpitations, tachycardia, nausea, and significantly higher rates of esophageal cancer. The genetic conditions underlying alcohol flush is very frequent (30-50%) in East Asian populations.

Due to the lack of tools by which emergency physicians can manage and/or eliminate toxic substances (such as alcohol), there is an urgent need to address the growing number of deaths by substance or alcohol poisoning with novel therapies.

SUMMARY

In one aspect, the present disclosure describes a formulation of a system of enzymes and co-factors encapsulated in microparticles such as liposomes for rapid elimination of a toxic or undesirable molecule from an environment, such as for eliminating ethanol from the blood of a subject. In one embodiment, the enzyme system comprises alcohol dehydrogenase (ADH), acetaldehyde dehydrogenase (ALDH), and NADH oxidase (NOX). In one embodiment, NADH oxidase is the only NAD+ regenerating enzyme present in the microparticles. In one embodiment the co-factor is nicotinamide adenine dinucleotide ($NAD^+$). In one embodiment, the enzymes and co-factor rapidly oxidize ethanol to acetate while regenerating the $NAD^+$ cofactor required to sustain the enzymatic reactions. In one embodiment, by encapsulating the enzymes in a microparticles, the enzymes are protected from serum proteases and physically removed from off-target ligands. In one embodiment, the co-localization of the enzymes in the microparticle lumen improves the kinetic rate of reaction and provides high concentrations of $NAD^+$. In one embodiment, encapsulation of the enzymes in microparticles such as but not limited to liposomes can be accomplished by various techniques generally known in the art such as thin-film hydration, inverted emulsion, or microfluidics. In one embodiment, the microparticle membrane is formulated so as to retain enzymes and the $NAD^+$ cofactor but allows for diffusion of ethanol, water, oxygen, and acetic acid across the membrane. In one embodiment, the microparticles can be injected intravenously into the bloodstream of patients to selectively remove ethanol, thereby providing therapeutic effect for cases of alcohol poisoning. Variations of the formulation disclosed herein can be used to treat other forms of acute poisoning.

In one embodiment, the present disclosure provides a microparticle-encapsulated system comprising $NAD^+$ and NADH oxidase (NOX), in combination with one or more enzymes capable of depleting levels of a substrate that is undesirably present in an environment. In one embodiment, the one or more enzymes are oxidases or dehydrogenases. In one embodiment, NADH oxidase is the only NAD+ regenerating enzyme present in the microparticles. In one embodiment, the substrate diffuses into the microparticle, is converted by the system disclosed herein to a different compound, such as a less toxic one, which can then diffuse out of the microparticle. In one embodiment, the microparticles can be injected in vivo to reduce high concentrations of a toxic compound. In one embodiment, the microparticles can be used in environmental locations for reducing levels of pollutants or other toxic compounds in, for example, water supply systems. Other uses include the food industry, in the manufacture (e.g. bioreactors), packaging and storage of foodstuffs.

In another embodiment, the present disclosure provides a method for making a composition of microparticle for removing toxic or undesirable molecules from an environment, the microparticle comprises a lipid bilayer phase and an aqueous phase, wherein the aqueous phase comprises (i) a system of generating $NAD^+$ from NADH, and (ii) one or more enzymes that are involved in one or more $NAD^+$-dependent reactions that remove the toxic or undesirable molecules from the environment. In one embodiment, the microparticles are liposomes. In one embodiment, NADH oxidase is the only NAD+ regenerating enzyme present in the microparticles.

In another embodiment, the present disclosure provides a method for removing a toxic or undesirable molecule from an environment, comprising the step of administering to the environment a composition of microparticle, the microparticle comprises an aqueous phase, wherein the aqueous phase comprises (i) a system of generating $NAD^+$ from NADH, and (ii) one or more enzymes that are involved in one or more $NAD^+$-dependent reactions that remove the toxic or undesirable molecules from the environment. In one embodiment, the method is used to remove ethanol from the blood of a human or an animal. In one embodiment, the toxic or undesirable molecule is ethanol, and the enzymes encapsulated in the liposomes comprise alcohol dehydrogenase (ADH) and acetaldehyde dehydrogenase (ALDH). In one embodiment, the microparticles comprise NADH oxidase. In one embodiment, NADH oxidase is the only NAD+ regenerating enzyme present in the microparticle.

In another embodiment, the present disclosure provides a composition of microparticle for removing toxic or undesirable molecules from an environment, the microparticle comprises an aqueous phase, wherein the aqueous phase comprises (i) a system of generating $NADP^+$ from NADPH, and (ii) one or more enzymes that are involved in one or more $NADP^+$-dependent reactions that remove the toxic or undesirable molecules from the environment. In one embodiment, the microparticles are liposomes. In one embodiment, NADPH oxidase is the only NADPH regenerating enzyme present in the microparticles.

In another embodiment, the present disclosure provides a method for making a composition of microparticle for removing toxic or undesirable molecules from an environment, the microparticle comprises an aqueous phase, wherein the aqueous phase comprises (i) a system of generating $NADP^+$ from NADPH, and (ii) one or more enzymes that are involved in one or more $NADP^+$-dependent reactions that remove the toxic or undesirable molecules from the environment. In one embodiment, the microparticles are liposomes. In one embodiment, NADPH oxidase is the only NADPH regenerating enzyme present in the microparticles.

In another embodiment, the present disclosure provides a method for removing a toxic or undesirable molecule from an environment, comprising the step of administering to the environment a composition of microparticles, the microparticles comprising an aqueous phase, wherein the aqueous phase comprises (i) a system of generating $NADP^+$ from NADPH, and (ii) one or more enzymes that are involved in one or more $NADP^+$-dependent reactions that remove the toxic or undesirable molecules from the environment. In one embodiment, the microparticles are liposomes. In one embodiment, NADPH oxidase is the only NADPH regenerating enzyme present in the microparticles.

In any of the foregoing embodiments, microparticles includes nanoparticles, liposomes, microparticles, microcapsules, microspheres and emulsions.

These and other aspects of the invention will be appreciated from the ensuing descriptions of the figures and detailed description of the invention.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DETAILED DESCRIPTION

As used herein, the terms "comprise", "comprises", "comprising", "includes", "including", "having" and their conjugates mean "including but not limited to".

As used herein, the term "consisting of" means "including and limited to".

As used herein, the term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "an enzyme" or "at least one enzyme" may include a plurality of enzymes, including mixtures thereof.

Throughout this application, various embodiments of the present disclosure may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral)

within the indicated range. The phrases "ranging/ranges between" a first indicate number and a second indicate number, and "ranging/ranges from" a first indicate number "to" a second indicate number, are used herein interchangeably and are meant to include the first and second indicated numbers and all the fractional and integral numerals therebetween.

When values are expressed as approximations, by use of the antecedent "about," it is understood that the particular value forms another embodiment. All ranges are inclusive and combinable. In one embodiment, the term "about" refers to a deviance of between 0.1-5% from the indicated number or range of numbers. In another embodiment, the term "about" refers to a deviance of between 1-10% from the indicated number or range of numbers. In another embodiment, the term "about" refers to a deviance of up to 20% from the indicated number or range of numbers. In one embodiment, the term "about" refers to a deviance of ±10% from the indicated number or range of numbers. In another embodiment, the term "about" refers to a deviance of ±5% from the indicated number or range of numbers.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting. Each literature reference or other citation referred to herein is incorporated herein by reference in its entirety.

The present disclosure describes a formulation of a system of enzymes and co-factors encapsulated in microparticles for rapid elimination of a toxic or undesirable molecule from an environment, such as for eliminating ethanol from the blood of a subject. "Microparticles" as used herein includes any vesicle or microparticle-based system that comprises a surface or membrane and an inner space, but also encompasses any other or larger particle comprising a membrane or surface of any composition. In one embodiment the microparticles are liposomes. Various aspects of the components and uses of the microparticles are described below.

Environments

An environment as described herein is any location where the microparticles of the invention may be placed or located to carry out their intended function. Such an environment may be but is not limited to the bloodstream, the circulation, the intestinal tract, a subcutaneous or intraperitoneal location, a bioreactor, a chemical reaction chamber, a storage vat, a pipe, a food container, a food preparation vessel or any other container or location where the reduction or removal of a compound is desirable, the compound capable of being converted to another compound by a microparticle of the invention as described herein. For example, for administration into the bloodstream, nanoparticles are preferred for lack of toxicity. For oral or intraperitoneal use, a larger microparticle may be provided. For environmental uses, larger microparticles may be provided. As will be described below, because the NOX system described herein for regenerating NAD+ is oxygen dependent, the dimensions of the particulate composition of the invention, the concentration of the composition at the desired site of activity, the desired rate of activity of the enzyme system, and the oxygen concentration at the site will provide guidance as to the preferred size of the particles for achieving the desired purpose.

Microparticles

The compositions and methods described herein are based upon a microparticle composition comprising the enzyme systems described elsewhere herein. The term "microparticles" as generally used herein includes any vesicle or microparticle-based system that comprises a lipid bilayer phase and an aqueous phase, but also encompasses any other or larger particle comprising a membrane and interior of any composition. In one embodiment the microparticles are polymer microparticles. In another embodiment, the microparticles are liposomes. Thus, microparticles includes but is not limited to nanoparticles, liposomes, microcapsules, microspheres and emulsions. Microparticles as generally used herein also includes the usual definition of microparticles. Because of their submicroscopic size, microparticles have unique material characteristics, and manufactured microparticles may find practical applications in a variety of areas, including medicine, engineering, catalysis, and environmental remediation. As described here, a microparticle has a surface comprising a membrane or lipid bilayer phase, and an inner phase or interior sometimes called a lumen. The lumen may be an aqueous phase. The lumen or aqueous phase may comprise a polymer or polymeric matrix. The lumen may be a liquid, a gel such as a hydrogel, or a solid. The viscosity, porosity and other characteristics of the lumen may be prepared to optimize the desired function of the microparticles. In some embodiments, the microparticles are 0.025 micrometers to 100 micrometers in size.

Non-limiting examples of the various types of microparticles embodied herein are described below. As will be noted in the descriptions of the various selections of sizes and types of microparticles, the microparticles may be from about 1 nm up to about 100 micrometers in size.

Nanoparticles. As it is generally understood in the art, nanoparticles are ultrafine particles with dimensions measured in nanometers (nm; $1 \text{ nm}=10^{-9}$ meter). Nanoparticles exist in the natural world and are also created as a result of human activities. In some embodiments, all three Cartesian dimensions of a nanoparticle are less than 100 nm. In another definition, nanoparticle is defined as a nano-object where only one of its characteristic dimensions is in the range of 1-100 nm, even if its other dimensions are outside that range. The lower limit of 1 nm is used because atomic bond lengths are reached at 0.1 nm. The size range—from 1 to 100 nm—overlaps considerably with that previously assigned to the field of colloid science—from 1 to 1,000 nm.

Thus, it is not uncommon to find literature that refers to nanoparticles and colloidal particles in equal terms. The difference is essentially semantic for particles below 100 nm in size. In some embodiments, the nanoparticle has an average diameter that ranges from about 25 nm, or from about 50 nm up to about 200 nm, or up to about 150 nm, or up to about 100 nm. In another embodiment, the nanoparticle preferred average diameter is less than about 100 nm.

Microparticles. Microparticles can be classified according to their size, shape, and material properties. Some classifications distinguish between organic and inorganic microparticles; the first group includes dendrimers, liposomes, and polymeric microparticles, while the latter includes fullerenes, quantum dots, and gold microparticles. Other classifications divide microparticles according to whether they are carbon-based, ceramic, semiconducting, or polymeric. The way in which microparticles are classified typically depends on their application, such as in diagnosis or therapy versus basic research, or may be related to the way in which they were produced. In one embodiment, the microparticles are about from 1 micrometer to about 10 micrometers. In one embodiment, microparticles can be nanoparticles of less than 1 micrometer in size.

Liposomes. A liposome is a spherical-shaped vesicle that is composed of one or more phospholipid bilayers, which closely resembles the structure of cell membranes. The ability of liposomes to encapsulate hydrophilic or lipophilic drugs has allowed these vesicles to become useful drug delivery systems. Liposomes are relatively stable; their aqueous phase may contain the hydrophilic drugs and their phospholipid bilayer may localize the lipophilic drugs. Moreover, their surface-modifiable characteristics have extended the liposomes' application to targeting and environmental sensitive delivery system. Various structural variations in the head, tail and bond of lipid molecules have been employed to develop different functionalized liposomes-based drug delivery systems.

Liposomes are most often composed of phospholipids, especially phosphatidylcholine, but may also include other lipids, such as egg phosphatidylethanolamine, so long as they are compatible with lipid bilayer structure. The phospholipid bilayers of a liposome can originate from natural sources, which are biologically inert, immunogenic and exhibit a lower inherent toxicity. A liposome design may also employ surface ligands that target them to a specified tissue.

Liposomes can vary in size from about 0.025 micrometers (μm) up to about 100 μm vesicles. In order to determine the half-life of liposomes, researchers must consider both the size and number of bilayers present within the liposome, as both of these properties play a role in determining the drug encapsulation volume of liposomes.

Liposomes can be classified as multilamellar vesicles or unilamellar vesicles, which can be further classified as giant unilamellar vesicle (GUV), large unilamellar vesicles (LUV) or small unilamellar vesicles (SUV), depending on their diameter. Unilamellar vesicles contain a single phospholipid bilayer sphere that encloses the aqueous solution, whereas multilamellar liposomes will exhibit multiple phospholipid bilayers.

The hydrophilic solutes dissolved in the aqueous solution core of liposome cannot readily pass through the lipid bilayer. Hydrophobic chemicals associate with the bilayer. A liposome can be hence loaded with hydrophobic and/or hydrophilic molecules.

Various amphiphilic lipids can form bilayers in an aqueous environment to encapsulate the enzyme systems described herein as a liposome. These lipids can have an anionic, cationic or zwitterionic hydrophilic head group. Some phospholipids are anionic whereas other are zwitterionic. Suitable classes of phospholipid include, but are not limited to, diacylglyceride compounds such as phosphatidylethanolamines, phosphatidylcholines, phosphatidylserines, and phosphatidylglycerols. Non-limiting examples of phospholipids include phosphatidic acid (phosphatidate), phosphatidylethanolamine (cephalin), phosphatidylcholine (lecithin), phosphatidylserine, phosphoinositides such as phosphatidylinositol, phosphatidylinositol phosphate, phosphatidylinositol bisphosphate and phosphatidylinositol trisphosphate; and phosphosphingolipids such as ceramide phosphorylcholine, ceramide phosphorylethanolamine and ceramide phosphoryllipid.

Non-limiting examples of phospholipids include 1,2-dierucoyl-sn-glycero-3-phosphate (sodium salt), 1,2-dierucoyl-sn-glycero-3-phosphocholine, 1,2-dierucoyl-sn-glycero-3-phosphoethanolamine, 1,2-dierucoyl-sn-glycero-3 (phospho-rac-(1-glycerol) (sodium salt), 1,2-dilinoleoyl-sn-glycero-3-phosphocholine, 1,2-dilauroyl-sn-glycero-3-phosphate (sodium salt), 1,2-dilauroyl-sn-glycero-3-phosphocholine, 1,2-dilauroyl-sn-glycero-3-phosphoethanolamine, 1,2-dilauroyl-sn-glycero-3(phospho-rac-(1-glycerol) (sodium salt), 1,2-dilauroyl-sn-glycero-3(phospho-rac-(1-glycerol) (ammonium salt), 1,2-dilauroyl-sn-glycero-3-phosphoserine (sodium salt), 1,2-dimyristoyl-sn-glycero-3-phosphate (sodium salt), 1,2-dimyristoyl-sn-glycero-3-phosphocholine, 1,2-dimyristoyl-sn-glycero-3-phosphoethanolamine, 1,2-dimyristoyl-sn-glycero-3 (phospho-rac-(1-glycerol) (sodium salt), 1,2-dimyristoyl-sn-glycero-3(phospho-rac-(1-glycerol) (ammonium salt), 1,2-dimyristoyl-sn-glycero-3(phospho-rac-(1-glycerol) (sodium/ammonium salt), 1,2-dimyristoyl-sn-glycero-3-phosphoserine (sodium salt), 1,2-dioleoyl-sn-glycero-3-phosphate (sodium salt), 1,2-dioleoyl-sn-glycero-3-phosphocholine, 1,2-dioleoyl-sn-glycero-3-phosphoethanolamine, 1,2-dioleoyl-sn-glycero-3(phospho-rac-(1-glycerol) (sodium salt), 1,2-dioleoyl-sn-glycero-3-phosphoserine (sodium salt), 1,2-dipalmitoyl-sn-glycero-3-phosphate (sodium salt), 1,2-dipalmitoyl-sn-glycero-3-phosphocholine, 1,2-dipalmitoyl-sn-glycero-3-phosphoethanolamine, 1,2-dipalmitoyl-sn-glycero-3(phospho-rac-(1-glycerol) (sodium salt), 1,2-dipalmitoyl-sn-glycero-3(phospho-rac-(1-glycerol) (ammonium salt), 1,2-dipalmitoyl-sn-glycero-3-phosphoserine (sodium salt), 1,2-distearoyl-sn-glycero-3-phosphate (sodium salt), 1,2-distearoyl-sn-glycero-3-phosphocholine, 1,2-distearoyl-sn-glycero-3-phosphoethanolamine, 1,2-distearoyl-sn-glycero-3(phospho-rac-(1-glycerol) (sodium salt), 1,2-distearoyl-sn-glycero-3(phospho-rac-(1-glycerol) (ammonium salt), 1,2-distearoyl-sn-glycero-3-phosphoserine (sodium salt), egg-phosphatidylcholine, hydrogenated Egg phosphatidylcholine, hydrogenated Soy phosphatidylcholine, 1-myristoyl-sn-glycero-3-phosphocholine, 1-palmitoyl-sn-glycero-3-phosphocholine, 1-stearoyl-sn-glycero-3-phosphocholine, 1-myristoyl-2-palmitoyl-sn-glycero 3-phosphocholine, 1-myristoyl-2-stearoyl-sn-glycero-3-phosphocholine, 1-palmitoyl-2-myristoyl-sn-glycero-3-phosphocholine, 1-palmitoyl-2-oleoyl-sn-glycero-3-phosphocholine, 1-palmitoyl-2-oleoyl-sn-glycero-3-phosphoethanolamine, 1-palmitoyl-2-oleoyl-sn-glycero-3(phospho-rac-(1-glycerol) . . . ] (sodium salt), 1-palmitoyl-2-stearoyl-sn-glycero-3-phosphocholine, 1-stearoyl-2-myristoyl-sn-glycero-3-phosphocholine, 1-stearoyl-2-oleoyl-sn-glycero-3-phosphocholine and 1-stearoyl-2-palmitoyl-sn-glycero-3-phosphocholine. Phospholipids and other components for making microparticles described herein may be purchased from Avanti Polar Lipids, Inc., Alabaster, Ala.

Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC and dodecylphosphocholine. The lipids can be saturated or unsaturated.

The foregoing description of microparticles is not intended to be limiting, and variations are embraced herein that allow the operation of the enzyme systems described herein to operate in a membrane-bound particle to carry out the desired reactions. As noted here, there is overlap in the definitions of the different microparticles with regard to sizes, relative dimensions, membrane compositions, internal compositions, and methods of manufacture. One of skill in the art will readily identify for the particular intended use, the appropriate size and composition of the microparticles to be able to be delivered to the environment, to carry out the intended function in that environment for an effective duration, and then to degrade or be eliminated safely from that environment. Such variations in composition and size are within the scope of the embodiments described herein.

Thus, by way of non-limiting examples, the microparticles among the various types described here may have a size of from about 1 nm to about 100 micrometers, from about 10 nm to about 100 micrometers, from about 10 nm to about 1 micrometer, from about 10 nm to about 100 micrometers, from about 25 nm to about 1 micrometer, from about 25 nm to about 10 micrometers, from about 25 nm to about 100 micrometers, from about 1 nm to about 10 micrometers, from about 1 nm to about 1 micrometer, from about 1 nm to about 500 nm, from about 10 nm to about 500 nm, from about 1 micrometer to about 100 micrometers or from about 10 micrometers to about 100 micrometers. In some embodiments, the microparticles of the various types described herein may be about 1 nm or larger, about 10 nm or larger, about 25 nm or larger, about 100 nm or larger, about 500 nm or larger, about 1 micrometer or larger, or about 10 micrometers or larger. In some embodiments, the microparticles of the various types described herein may be about 100 micrometers or smaller, about 10 micrometers or smaller, about 1 micrometer or smaller, about 500 nm or smaller, about 100 nm or smaller, about 25 nm or smaller, or about 10 nm or smaller. These are merely exemplary size ranges and limits and are not intended to be limiting.

Microparticle-Based Technologies. In general, microparticle-based technologies have the advantages of improving the efficiency, sustainability, and/or speed of already-existing processes. The microparticle-encapsulated enzyme systems disclosed herein can be incorporated into various technologies described below. The small size of microparticles is especially advantageous in medicine. Microparticles can not only circulate widely throughout the body but also enter cells or be designed to bind to specific cells. Those properties have enabled new ways of enhancing images of organs, tumors and other diseased tissues in the body. In one embodiment, microparticles of the invention comprising an enzyme system can be delivered to cells, for example, to function essentially as an organelle that converts or detoxifies an intracellular or extracellular compound or metabolite. In one embodiment, the microparticle improves upon or replaces a missing enzymatic pathway in a cell, e.g., a congenital deficiency, thus restoring normal metabolism.

The NAD$^+$ and NADH System

Nicotinamide adenine dinucleotide (NAD) is a cofactor that is central to metabolism. NAD is a dinucleotide consisting of two nucleotides joined through their phosphate groups. One nucleotide contains an adenine nucleobase and the other nicotinamide. NAD exists in two forms: an oxidized and reduced form, abbreviated as NAD$^+$ and NADH respectively. NADH oxidase (or NADH dehydrogenase) is an iron-sulfur-containing flavoprotein that reversibly oxidizes NADH to NAD$^+$.

In metabolism, NAD is involved in redox reactions, carrying electrons from one reaction to another. The cofactor is, therefore, found in two forms in cells: NAD$^+$ is an oxidizing agent; it accepts electrons from other molecules and becomes reduced. This reaction forms NADH, which can then be used as a reducing agent to donate electrons. These electron transfer reactions are the main function of NAD. However, it is also used in other cellular processes, for example, as a substrate of enzymes that add or remove chemical groups from proteins, in posttranslational modifications etc.

Some NAD is converted into the coenzyme nicotinamide adenine dinucleotide phosphate (NADP). The chemistry of NADP is similar to that of NAD, but it has different role, being predominantly a cofactor in anabolic metabolism. In some embodiments herein, the NADPH/NADP$^+$ system is employed in an analogous manner to the NADH/NAD$^+$ system, in combination with NADPH oxidase and one or more detoxifying enzymes.

NADH, the reduced form of NAD$^+$, facilitates numerous biological reactions. It works as a reducing agent and is oxidized while reducing the other compound. NADH is necessary for cellular development and energy production. It is essential for producing energy from food and is the principal carrier of electrons in the energy-producing process in the cells. NADH is also an important antioxidant.

NADH also acts as a co-factor for many enzymes such as alcohol dehydrogenase, acetaldehyde dehydrogenase, and many others.

For use in the methods and compositions described herein, NOX may be derived or obtained from any number of sources. In one embodiment, the NOX is derived from *Streptococcus pyogenes*.

Alcohol Dehydrogenase (ADH)

ADH are a group of dehydrogenase enzymes that occur in many organisms and facilitate the interconversion between alcohols and aldehydes or ketones with the reduction of nicotinamide adenine dinucleotide (NAD+) to NADH. In humans and many other animals, they serve to break down alcohols that otherwise are toxic, and they also participate in generation of useful aldehyde, ketone, or alcohol groups during biosynthesis of various metabolites. In yeast, plants, and many bacteria, some alcohol dehydrogenases catalyze the opposite reaction as part of fermentation to ensure a constant supply of NAD+.

ADH may be derived from any species, such as but not limited to bacteria, yeast, plants, and mammals. It may be expressed recombinantly. In one embodiment, the ADH is derived from *Saccharomyces cerevisiae*.

Acetaldehyde Dehydrogenase (ALDH)

ALDH is an oxidoreductase that catalyzes the conversion of acetaldehyde into acetic acid. In humans, there are three known genes which encode this enzymatic activity, ALDH1A1, ALDH2, and the more recently discovered ALDH1B 1 (also known as ALDH5). These enzymes are members of the larger class of aldehyde dehydrogenases.

ALDH may be derived from any species, such as but not limited to bacteria, yeast, plants, and mammals. It may be expressed recombinantly. In one embodiment, ALDH is derived from humans (*Homo sapiens*).

$NADP^+$ and NADPH System

Nicotinamide adenine dinucleotide phosphate ($NADP^+$) is a cofactor used in anabolic reactions, such as the Calvin cycle and lipid and nucleic acid syntheses, which require NADPH as a reducing agent. It is used by all forms of cellular life. NADPH is the reduced form of $NADP^+$. $NADP^+$ differs from $NAD^+$ in the presence of an additional phosphate group on the 2' position of the ribose ring that carries the adenine moiety. This extra phosphate is added by $NAD^+$ kinase and removed by $NADP^+$ phosphatase.

NADPH provides the reducing equivalents for biosynthetic reactions and the oxidation-reduction involved in protecting against the toxicity of reactive oxygen species (ROS), allowing the regeneration of glutathione (GSH). NADPH is also used for anabolic pathways, such as cholesterol synthesis and fatty acid chain elongation.

The NADPH system is also responsible for generating free radicals in immune cells by NADPH oxidase. These radicals are used to destroy pathogens in a process termed the respiratory burst. It is the source of reducing equivalents for cytochrome P450 hydroxylation of aromatic compounds, steroids, alcohols, and drugs.

NADPH oxidase in some instances is a membrane-bound enzyme complex that faces the extracellular space. It can be found in the plasma membrane as well as in the membranes of phagosomes used by neutrophil white blood cells to engulf microorganisms. NADPH oxidase catalyzes the production of a superoxide free radical by transferring one electron to oxygen from NADPH. During this process $O_2$ is transported from the extracellular space to the cell interior and the $H^+$ is exported.

In animals, there are two types of NADPH oxidase: one in white blood cells (neutrophilic) and the other in vascular cells, differing in biochemical structure and functions. Neutrophilic NADPH oxidase produces superoxide almost instantaneously, whereas the vascular enzyme produces superoxide in minutes to hours. Moreover, in white blood cells superoxide has been found to transfer electrons across the membrane to extracellular oxygen, while in vascular cells the radical anion appears to be released mainly intracellularly. In microparticles of the invention incorporating the NADPH oxidase system, additional enzymes to convert superoxide to oxygen may be included, to recycle oxygen as well. Enzymes such as but not limited to superoxide dismutase and catalase may be included. In some instances, NADPH oxidase can be mutated to oxidize NADH instead, and vice versa. This ability to alter ligand specificity of these enzymes points to the similarity of NADH and NADPH.

Other Components

In addition to the microparticle components described herein, such microparticles may comprise one or more other components to enhance the intended function. In one embodiment, agents such as a crowding agent may be included to enhance the interaction between the enzymes of the microparticle when present at high concentrations, to assure the efficiency of the enzymatic processes. In one embodiment, the crowding agent polyethylene glycol may be included in the microparticle. In one embodiment, the ratios of the enzymes in the microparticle may be modified and optimized by the presence of a crowding agent.

In another embodiment, oxygen affinity and diffusion within the microparticle may be improved by including an agent in or on the microparticles that enhances oxygen affinity or diffusion. In one embodiment, an oxygen diffusion-enhancing compound such as but not limited to crocetin and trans sodium crocetinate, may be used. Oxygen carrying molecules such as heme may also be used.

In another embodiment, transport of the substrate into the microparticle, transport of the product out of the microparticle, or transport of a cofactor into the microparticle may be facilitated by incorporation of a channel protein in the membrane or wall of the microparticle. In some non-limiting embodiments, channel proteins include alpha haemolysin from *Staphylococcus aureus*, which has been shown to enable passive diffusion through its pores; csgG from *E. coli* used to enable DNA sequencing; SatP from *Citrobacter koseri* which unidirectionally translocates acetate; and the passive pores MspA and ClyA. In one embodiment, a selective or non-selective pore may be prepared using DNA origami. In some embodiments, non-limiting examples of active transporters include YaaH in *E coli*, a succinate-acetate transporter; ADY2 in *S cerevisiae*, an acetate transporter; the acetate/cation symporter actP; mammalian solute carrier transporters, and ABC transporters.

In another embodiment, the permeability of the membrane or wall to the substrate, product, oxygen, co-factors, or other components can be altered in a number of ways, such as but not limited to changing the cholesterol:phospholipid ratio, the identity of the phospholipid, the ratio of different phospholipids, and the presence of proteins (e.g. channel proteins) in the membrane, the incorporation of polymers, as described above.

In another embodiment, the microparticle may comprise any other cofactors/electron carriers that participate in or enhance the reaction within the microparticle. Non-limiting examples include pyrroloquinoline quinones, flavin adenine dinucleotide (FAD), flavin mononucleotide (FMN), iron-sulfur clusters, and heme groups.

In one embodiment, moieties such as polyethylene glycol (PEG) can be conjugated to the head groups on the exterior of the liposomes, thus preventing opsonization of the liposomes and clearance by immune cells, thereby increasing the half-life of the liposomes. Other such molecular groups that can be conjugated to liposome surfaces to achieve a desired effect include other polymers (e.g. polyvinyl alcohol, cellulose, chitin, polylactic-co-glycolic acid), hydrogels (e.g. agarose), proteins (e.g. albumin), small molecules, DNA, RNA, or secondary shells of lipids or phospholipids.

In another embodiment, one or more of the enzymes in the microparticles may be a modified or mutant enzyme, or otherwise engineered to optimally function at the same pH and ionic strength as the other enzymes in the microparticle. Enzymes used in the systems described herein can be engineered by various means for improved performance, including wider or different optimums for pH, temperature, and ambient salt concentration, improved catalytic rates (Kcat, Vmax, turnover rate etc), ligand affinity (Km), robustness to the presence of hydrophobic molecules, ligand (substrate) specificity, covalent and non-covalent association with other macromolecules and structure. Means of engineering enzymes include: random mutation, directed evolution towards the features listed above, random or non-random shuffling of enzyme gene DNA within or between gene DNA of other enzymes, metagenomic library synthesis and hit screening, and rational engineering. In one embodiment, the one or more enzymes involved in degrading the toxic or undesirable molecule is modified. In one embodiment, the NADH oxidase is modified. In one embodiment the NADPH oxidase is modified.

In another embodiment, a buffer, salts, or other components in the aqueous medium may be included in the microparticles, such as but not limited to phosphate buffered saline or a potassium phosphate buffer. A salt such as sodium chloride may be included. One of skill in the art in formulating the enzymes in a particular microparticle will readily identify the components and factors such as optimal pH, ionic strength and buffer strength, such that each of the enzymes may operate its desired function within the milieu of the microparticle.

Enzyme Systems for the Removal of Toxic Molecules

In one embodiment, the present disclosure describes a formulation of a system of enzymes and co-factors encapsulated in microparticles for rapid elimination of a toxic or undesirable molecule from an environment (e.g. eliminating ethanol from the blood of a subject). As noted herein, "microparticles" as used herein includes any vesicle or microparticle-based system that comprises a lipid bilayer phase and an aqueous phase, but also encompasses any other or larger or smaller particle comprising a membrane of any composition. In one embodiment the microparticles are polymer microparticles. In another embodiment, the microparticles are liposomes. Preparation of liposomes is well-known in the art and liposomes are typically, though not exclusively, composed of phospholipid bilayers. A phospholipid is an amphiphilic molecule typically consisting of a hydrophilic phosphate head group and two hydrophobic lipid chains. Phospholipids comprise the majority of cell membranes and self-aggregate into bilayers that make up liposomes. Liposomes can be composed of other amphiphilic molecules. In one embodiment, the liposomes can be formulated from art-recognized basic components, such as but not limited to, phospholipid POPC and cholesterol. For example, the liposomes can comprise phospholipids, cholesterol, conjugated phospholipids, small molecule adjuvants such as QS21 and saponins, cationic lipids internal or external to the liposome, and any combination thereof. In another embodiment, the liposomes may include peptide vesicles, such as amphiphilic peptides instead of phospholipids. Among other embodiments, micelles, capsosomes, exosomes, and ethosomes are embodied herein.

Figure 1:
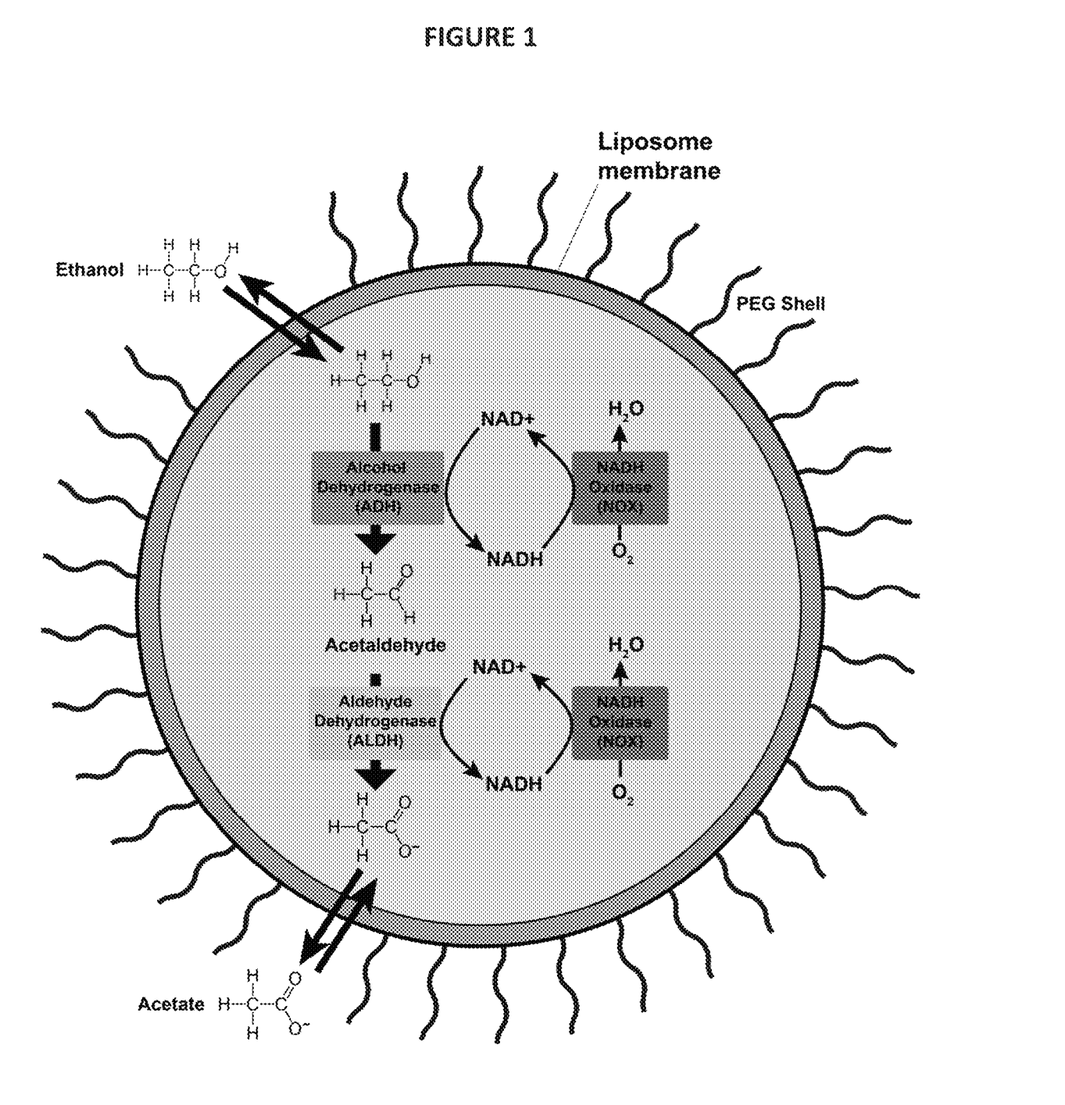
FIG. 1 depicts one embodiment of a formulation useful for elimination of ethanol from the blood. The formulation comprises microparticles that contain alcohol dehydrogenase (ADH), acetaldehyde dehydrogenase (ALDH), NADH oxidase (NOX) and $NAD^+$. The microparticles comprise a liposome covered with a polyethylene glycol shell.

In one embodiment, the present disclosure describes a therapeutic formulation that enhances elimination of ethanol from the blood (FIG. 1). In one embodiment, the formulation comprises microparticles such as liposomes that contain alcohol dehydrogenase (ADH), acetaldehyde dehydrogenase (ALDH), and NADH oxidase (NOX). The co-factor $NAD^+$ is also present. In one embodiment, the following enzymes and reactions occur in a microparticle to convert ethanol to acetate:

ADH: $EtOH + NAD^+ \rightarrow NADH + Acetaldehyde + H^+$

ALDH: $Acetaldehyde + H_2O + NAD^+ \rightarrow NADH + Acetate + H^+$

NOX: $2NADH + 2H^+ + O_2 \rightarrow NOX \rightarrow 2NAD^+ + 2H_2O$.

As will be seen in the examples herein, the aforementioned enzyme system produces $NAD^+$ from NADH using ambient oxygen, thus continuously supplying $NAD^+$ to carry out the oxidation reactions, without the need for additional $NAD^+$. Thus, the conversion of ethanol to acetate is not limited by the number of $NAD^+$ molecules in the microparticle, as they are continuously recycled or regenerated. Thus, in one embodiment, cofactor recycling by NOX and oxygen, coupled to the oxidation reactions converting ethanol to acetate, enables the continuous conversion of ethanol to acetate. In one embodiment, NOX maintains the $NAD^+$ levels in the microparticle. In one embodiment, NOX maintains the $NAD^+$ levels in the microparticle at or near the initial concentration. In one embodiment, the enzyme system converts ethanol to acetate until at least one component other than $NAD^+$ becomes limiting.

As used herein, the term "encapsulation" refers to the containment of molecules within the lumen (the space on the interior of the membrane) of a particle or vesicle. Encapsulation protects the enzymes from blood serum proteases and opsonization. It also prevents the patient's immune system from reacting strongly to the presence of large amounts of heterologous protein in the blood. By co-localizing the enzymes in the liposome, their effective concentrations are increased, thereby yielding significantly higher kinetic rates of turnover. Similarly, containing $NAD^+$ at high concentrations in the liposomes enables faster rates of ethanol and acetaldehyde turnover (due to higher frequency of ligand binding). The liposome membrane also keeps out off-target ligands of ADH and ALDH that are present in the blood, thereby ensuring no endogenous metabolites are metabolized or eliminated. ADH is promiscuous and can oxidize a variety of primary alcohols, some even preferentially to the target molecule (ethanol in this case). These ligand molecules include certain vitamins and other important endogenous metabolites that are abundant in blood. These metabolites tend to be large and unable to penetrate the microparticle boundaries by diffusion. By encapsulating ADH in the microparticle, these metabolites are physically separated from ADH. This ensures that ADH does not oxidize important metabolites in the blood, which makes the formulation safer to use than free enzyme. This is similarly true for ALDH and endogenous aldehydes. Liposomes can range from ~20 nm to several 1000 nm in size. Their utility for different applications is affected by their size. Larger liposomes (e.g. >300 nm) are rapidly cleared from the blood by the liver and spleen. Smaller liposomes (e.g. 20-200 nm) can persist in the blood for several days. Large liposomes can be implanted in different organs and act as "artificial cells" (see, for example, Chang et al., Therapeutic applications of polymeric artificial cells. Nature Reviews Drug Discovery 4:221-245 (2005)). In addition to size, the most important feature of a liposome is its membrane composition. In one embodiment, moieties such as polyethylene glycol (PEG) can be conjugated to the head groups on the exterior of the liposomes, thus preventing opsonization of the liposomes and clearance by immune cells, thereby increasing the half-life of the liposomes. Other such molecular groups that can be conjugated to liposome surfaces to achieve a desired effect include other polymers (e.g. polyvinyl alcohol, cellulose, chitin, polylactic-co-glycolic acid), hydrogels (e.g. agarose), proteins (e.g. albumin), small molecules, DNA, RNA, or secondary shells of lipids or phospholipids.

In one embodiment, the present disclosure describes encapsulation of enzyme systems comprising NADH oxidase (NOX), an enzyme that oxidizes the co-factor NADH to NAD+ using molecular oxygen, thereby providing a means to sustain enzymatic oxidation reactions on any substrate for which at least one enzyme capable of oxidizing (dehydrogenating) the substrate, or optionally its oxidation products, is desired. In some embodiments, more than one enzyme is provided in the encapsulated system. NOX allows for the regeneration of NAD+ from NADH produced during the enzymatic oxidation of the substrate. Thus, by providing in a microparticle the components NOX, NAD+, and at least one oxidase or dehydrogenase for a target substrate, the concentration of the substrate required can be lowered by the enzyme system. Placing the microparticles in an environment containing the substrate, and letting the substrate diffuse into the microparticles, the substrate can be oxidized by the enzyme system and the products of the enzymatic reaction can then diffuse out of the microparticles. The NADH generated by the oxidation of the substrate is then oxidized by NOX, thus regenerating NAD+ levels to sustain the continuous oxidation of the substrate. The enzyme system may comprise a single enzyme that oxidizes the substrate, or may contain multiple enzymes that oxidize the product or products of the first or subsequent oxidation reactions. In one embodiment, the microparticles may contain other enzymes, for example, an enzyme that is not an oxidase or dehydrogenase, to further convert the products of the oxidation reaction(s) to another product or isomer of the product. In one embodiment, two enzymes are provided to convert a substrate, ethanol, into a less toxic product, acetate. Such an encapsulated NOX-based enzyme system may be useful for in vivo medical uses including veterinary uses, or for environmental purposes, in food processing, packaging and storage, or any other uses in which lowering of the concentration of a compound (substrate) in a particular environment is desired.

In one embodiment, the microparticles comprise only NADH oxidase as the NAD+ regenerating enzyme. In other embodiments, the microparticles comprise only NADPH oxidase as the NADP+ regenerating enzyme. Thus, in one embodiment, a method is provided for removing a toxic or undesirable molecule from an environment, comprising the step of administering to the environment a composition of microparticles, said microparticle comprises an aqueous phase, wherein said aqueous phase consists of (i) NADH oxidase (NOX) for generating NAD+ from NADH, and comprises (ii) one or more enzymes that are involved in one or more NAD+-dependent reactions that remove said toxic or undesirable molecules from said environment. In other embodiment, a method is provided for removing a toxic or undesirable molecule from an environment, comprising the step of administering to the environment a composition of microparticles, said microparticle comprises an aqueous phase, wherein said aqueous phase consists of (i) NADPH oxidase for generating NAPD+ from NADPH, and comprises (ii) one or more enzymes that are involved in one or more NAPD+-dependent reactions that remove said toxic or undesirable molecules from said environment.

The enzymes in the microparticle may be derived from native human and/or heterologous (non-human) sources and can be enzymes that have been engineered to maximize their catalytic rates, binding affinity to their target ligands, pH optima, solubility, or stabilized during encapsulation. In another embodiment the enzymes are engineered to optimally function at the same pH and ionic strength.

Enzymes used in the systems described herein can be engineered by various means for improved performance, including wider or different optimums for pH, temperature, and ambient salt concentration, improved catalytic rates (Kcat, Vmax, turnover rate etc), ligand affinity (Km), robustness to the presence of hydrophobic molecules (e.g. liposome membranes, organic solvents), ligand specificity, covalent and non-covalent association with other macromolecules (e.g. fusion to DNA or other proteins) and structure. Means of engineering enzymes include: random mutation, directed evolution towards the features listed above, random or non-random shuffling of enzyme gene DNA within or between gene DNA of other enzymes, metagenomic library synthesis and hit screening, and rational engineering (in which a structural biologists makes purposeful mutations in the enzyme structure to achieve a new characteristic).

For in vivo medical uses, the components or fabricated microparticles will have to be sterilizable. This and other requirements for the optimization of enzymes and other components would be readily achieved by one of skill in the art.

In some embodiments, the enzymes and co-factors that are provided in proper ratios are encapsulated in microparticles such as liposomes. The theoretical optimal enzyme molar ratio in each liposome is the molar ratio at which the turnover rate of the initial substrate (in one example, ethanol to acetaldehyde by ADH) is equal to the turnover rate of the final substrate (in the same example, acetaldehyde to acetate by ALDH) while maintaining a nearly constant supply of NAD+. In some embodiments, the ratio of ALDH to ALD is from about 1:1 to about 1000:1. In some embodiments, the ratio of ALDH to ALD is from about 10:1 to about 500:1. In some embodiments, the ratio of ALDH to ALD is from about 10:1 to about 100:1. In some embodiments, the ratio of ALDH to ALD is from about 60:1 to about 40:1. In some embodiments, the ratio of ALDH to ALD is about 45:1. In some embodiments, the ratio of NOX to ALD is from about 1000:1 to about 1:1. In some embodiments, the ratio of NOX to ALD is from about 500:1 to about 1:1. In some embodiments, the ratio of NOX to ALD is from about 100:1 to about 1:1. In some embodiments, the ratio of NOX to ALD is from about 50:1 to about 1:1. In some embodiments, the ratio of NOX to ALD is from about 10:1 to about 1:1. In some embodiments, the ratio of NOX to ALD is from about 5:1 to about 2:1. In some embodiments, the ratio of NOX to ALD is about 2:1. As noted here, while this non-limiting guidance assumes these ratios are provided by active enzymes in the microparticles, such ratios may not be those followed during manufacture of the microparticles.

In one embodiment, for *Saccharomyces cerevisiae* ADH, human ALDH, and *Streptococcus pyogenes* NOX, this molar ratio is 1:44:2 (ADH:ALDH:NOX) based on currently available kinetic parameters. The rate of lowering the circulating ethanol level by the microparticles comprising an enzyme formulation close to this ratio will be limited only by the mass of enzymes given to the patient and the slowest kinetic rate of the slowest enzyme (in this case, ALDH). In practice, different enzymes may have unequal stability in the liposomal formulation and may suffer from unfolding during processing. Also, the above theoretical ratio does not take into account variability in enzyme activity due to different temperatures, salt concentrations, pH, etc, nor stability of the enzymes and other components during manufacture including any required sterilization or testing process. Thus, the optimal molar ratio used during manufacturing must be determined empirically for the intended use, the encapsulation methodology, duration of storage before use, and other conditions, but will be readily determinable by one of skilled in the art. Following proper purification and pharmaceutical stabilization, the resulting microparticles are then injected, for example, intravenously into patients suffering from alcohol poisoning.

In one embodiment, the invention disclosed herein describes inclusion of NOX in the microparticle formulation. Inclusion of NOX eliminates the need to rely on ambient $NAD^+$, which cannot be sufficiently supplied in the blood. It also eliminates the need to use other regenerative enzyme systems, such as those based on lactate, malate, or pyruvate oxidation, which require a supply of those molecules as electron donors for $NAD^+$ reduction. Other enzymes have been used as a means of regenerating $NAD^+$ in similar systems. These enzymes, including lactate dehydrogenase, malate dehydrogenase, pyruvate dehydrogenase, and glycerol dehydrogenase, use other small molecules as electron donors to reduce $NAD^+$ to NADH. However, in these systems, the small molecule electron donors cannot be easily regenerated inside the microparticle and cannot penetrate the microparticle boundary. In these formulations, the reactions are therefore limited by the abundance of the small molecule electron donors inside the microparticle. Because oxygen can easily cross most microparticle boundaries and is rich in the blood, the NOX system described herein is not similarly limited. In one embodiment, injection into the blood ensures that there is sufficient molecular oxygen present to enable the NOX reaction to occur. In one embodiment, the chemical reactions of ADH, ALDH, and NOX only require ethanol and molecular oxygen as substrates and the only two products are water and acetate, of which ethanol and acetic acid (protonated acetate) can freely diffuse across the liposome membrane. Taken together with the other benefits of liposome encapsulation discussed above, the liposomal formulations described herein provide novel and unique advantages as compared to other compositions currently known in the art.

In certain embodiments, the electron acceptor regenerating system comprises the cofactor $NADP^+$ which is regenerated from reduced $NADP^+$ (NADPH) by the NADP oxidase. In some microparticles of the invention, the $NADP^+$/NADPH system serves as the sole or primary electron acceptor regenerating system that provides $NADP^+$ to enable enzymes to oxidize certain substrates of interest that can diffuse or be transported into the microparticle. In some embodiments, the $NADP^+$/NADPH system may be present together with the $NAD^+$/NADH system, where each electron acceptor cofactor is coupled with a different enzyme(s) to convert a substrate to a different or less toxic compound. When both cofactor systems are present together, either one may be the first system that the substrate encounters upon entry to the microparticles; its enzymatic reaction product is then acted on by the other system. In some embodiments, additional enzymes or components may be present, such as superoxide dismutase and catalase, to convert superoxide into oxygen.

Indication and Administration for Ethanol Removing Microparticles

In one embodiment, the ethanol reducing microparticles of the present invention can be administered to a subject intravenously with a saline drip, which is commonly administered in such cases to ensure the patient is hydrated. Microparticles can also be injected directly into the vein with a syringe. In another embodiment, the microparticles can be inhaled. In another embodiment, the microparticles can be administered subcutaneously or intraperitoneally. In one embodiment, the microparticles are administered orally. In one embodiment, the microparticles are administered via inhalation.

In one embodiment, the invention disclosed herein provides microparticle formulations and uses thereof for the elimination of ethanol in the blood. In another embodiment, the invention disclosed herein can be used to address excess amounts of acetaldehyde in the blood in the case of the "alcohol flush" condition. Moreover, because the condition that leads to alcohol flush (i.e. the ALDH2*2 mutation) also makes patients unable to rapidly produce nitric oxide from the prodrug glycerol trinitrate, which is given as a sublingual pill to alleviate angina, the invention disclosed herein may also be useful for patients with the indicated mutation who are suffering from heart disease and associated angina (chest pain). In another embodiment, the microparticles of the invention are useful in treating disulfiram-induced acetaldehyde toxicity, wherein elevated acetaldehyde may occur in an individual on disulfiram who then consumes ethanol. In one embodiment, microparticles for this purpose may comprise the ALDH and NOX enzymes, and not ADH.

In other embodiments, microparticles can be provided to remove methanol or isopropanol from the body. In other embodiments, microparticles can be provided to remove acetone or ethylene glycol from the body.

In one embodiment, the liposomes of the invention are administered to a subject having a blood-alcohol concentration from about 0.01 g/dL to about 0.8 g/dL, although the invention is not so limiting and the health care professional will readily assess the need of the patients for ethanol removal using the microparticles of the invention, as well as the appropriate amount and infusion rate of microparticles to achieve detoxification.

Other Enzyme Systems and Indications

In one embodiment, the microparticle formulations disclosed herein can become a platform technology for delivery of therapeutics (such as enzymes) that can address a wide variety of medical needs. In one embodiment, such delivery of therapeutics would lead to safer and more efficacious treatment. For example, the present invention of using microparticle-encapsulated homologous/heterologous enzymes to eliminate toxic compounds from the blood can be applied to a number of different poisoning indications. Numerous toxic molecules and xenobiotics can be detoxified by oxidation with known enzymes (oxidases or dehydrogenases) which can be included in the microparticles of the present invention together with the NOX-based, $NAD^+$ regenerating system (or $NADP^+$ regenerating system). Non-limiting examples of such molecules include strychnine, oleandrin, cardiac glycosides, digoxin, veratridine, aconitine, grayanotoxin, batrachotoxin, glutamate, cytotoxins, tetrodotoxin, organophosphates, formaldehyde, isopropanol, methanol, acetone, ethylene glycol, VX, sarin, saxitoxin, gonyautoxins and yessotoxins. Thus, encapsulating one or more of these enzymes in microparticles as described herein would provide an improved method of treating human or animals suffering from conditions that can be remedied by these enzymes. Moreover, applications in the environmental remediation and food safety fields will also benefit from the present disclosure.

As noted above, another enzyme system may require the cofactor $NADP^+$, which can be regenerated from reduced $NADP^+$ (NADPH) by the enzyme nicotinamide adenine dinucleotide phosphate oxidase (NADP oxidase).

In some cases, the target ligand of the enzyme (substrate) cannot diffuse freely across the microparticle membrane. In these cases, a specific transporter can be provided to transport the ligand into the interior of the microparticles and the same or different transporter can be provided to transport the inert product across the membrane and out of the microparticle. Thus, by engineering the microparticle membrane to incorporate specific transporters, one can further enable the formulations and systems disclosed herein to target a wider variety of molecules and treat a greater variety of poisoning indications.

In one embodiment, there is provided a method for removing a toxic or undesirable molecule from an environment, comprising the step of administering to the environment a composition of microparticle, the microparticle comprises a lipid bilayer phase and an aqueous phase, wherein the aqueous phase comprises (i) a system of generating $NAD^+$ from NADH, and (ii) one or more enzymes that are involved in one or more $NAD^+$-dependent reactions that remove the toxic or undesirable molecules from the environment. In one embodiment, the microparticles are liposomes. In one embodiment, the system for generating $NAD^+$ from NADH comprises NADH oxidase (NOX). In one embodiment, the system for generating $NAD^+$ from NADH consists of NADH oxidase (NOX). In one embodiment, the composition of microparticles can be applied to an environment such as a water supply system, a food packaging, or a subject's blood. The subject can be a human or animal. In one embodiment, the method is used to remove ethanol from the blood of a subject. In this case, the enzymes encapsulated in the microparticles include NOX, alcohol dehydrogenase (ADH) and acetaldehyde dehydrogenase (ALDH). In one embodiment, the ADH, ALDH and NOX are present in a ratio of 1:44:2. In one embodiment, the composition of microparticles can be administered to the subject intravenously or by inhalation.

In another embodiment, there is provided a composition of microparticle for removing toxic or undesirable molecules from an environment, the microparticle comprises a lipid bilayer phase and an aqueous phase, wherein the aqueous phase comprises (i) a system of generating $NAD^+$ from NADH, and (ii) one or more enzymes that are involved in one or more $NAD^+$-dependent reactions that remove the toxic or undesirable molecules from the environment. In one embodiment, the microparticles are liposomes. In one embodiment, the system of generating NAD+ from NADH comprises NADH oxidase (NOX). In one embodiment, the system of generating NAD+ from NADH consists of NADH oxidase (NOX). In one embodiment, when the composition is used to remove ethanol (e.g. remove ethanol from the blood of a subject), the enzymes encapsulated in the microparticles include NOX, alcohol dehydrogenase (ADH) and acetaldehyde dehydrogenase (ALDH). In one embodiment, the ADH, ALDH and NOX are present in a ratio of 1:44:2.

In another embodiment, there is provided a method for removing a toxic or undesirable molecule from an environment, comprising the step of administering to the environment a composition of microparticle, the microparticle comprises a lipid bilayer phase and an aqueous phase, wherein the aqueous phase comprises (i) a system of generating $NADP^+$ from NADPH, and (ii) one or more enzymes that are involved in one or more $NADP^+$-dependent reactions that remove the toxic or undesirable molecules from the environment. In one embodiment, the microparticles are liposomes. In one embodiment, the system of generating NADP+ from NADPH comprises NADPH oxidase. In one embodiment, the composition of microparticles can be applied to an environment such as a water supply system, a food packaging, or a subject's blood. The subject can be a human or animal.

In another embodiment, there is provided a composition of microparticle for removing toxic or undesirable molecules from an environment, the microparticle comprises a lipid bilayer phase and an aqueous phase, wherein the aqueous phase comprises (i) a system of generating $NADP^+$ from NADPH, and (ii) one or more enzymes that are involved in one or more NADP+-dependent reactions that remove the toxic or undesirable molecules from the environment. In one embodiment, the microparticles are liposomes. In one embodiment, the system of generating NADP+ from NADPH comprises NADPH oxidase. In one embodiment, the system of generating NADP+ from NADPH consists of NADPH oxidase. In one embodiment, the composition of microparticles can be applied to an environment such as a water supply system, a food packaging, or a subject's blood. The subject can be a human or animal.

In another embodiment, there is provided a method of making a composition of microparticle for removing toxic or undesirable molecules from an environment, the microparticle comprises a lipid bilayer phase and an aqueous phase, wherein the aqueous phase comprises (i) a system of generating $NADP^+$ from NADPH, and (ii) one or more enzymes that are involved in one or more NADP+-dependent reactions that remove the toxic or undesirable molecules from the environment. In one embodiment, the microparticles are liposomes. In one embodiment, the system of generating NADP+ from NADPH comprises NADPH oxidase. In one embodiment, the system of generating NADP+ from NADPH consists of NADPH oxidase. In one embodiment, the composition of microparticles can be applied to an environment such as a water supply system, a food packaging, or a subject's blood. The subject can be a human or animal.

Manufacturing of the microparticles described herein for the intended uses will be understood by one of skill in the art. For example, for use in alcohol poisoning, microparticles will be manufactured under good manufacturing practices (cGMP) currently in effect from the US Food and Drug Administration, or other national authorities. In one embodiment, a contract manufacturer with cleanroom facilities conducts the manufacturing, as well as acquisition of raw materials, identity testing, drafting master batch record, preparation of the microparticles, sterilization, filling, inspection, labeling, release testing. Stability testing will also be carried out to determine shelf life. cGMP manufacture of microparticles and liposomes is readily sourced by one of skill in the art. For other, industrial uses of the microparticles of the invention, corresponding manufacturing processes are readily identified. Non-limiting examples of liposome-based drugs and those in development, and manufacturing processes thereof include Bulbake et al, Pharmaceutics 2017, 9(2), 12; Webb et al., 2020, International Journal of Pharmaceutics, https://doi.org/10.1016/j.ijpharm.2020.119266; and Maherani et al., 2011, Nanoscience 7(3):436-457, each of which is incorporated herein in its entirety.

In the description presented herein, each of the steps of the invention and variations thereof are described. This description is not intended to be limiting and changes in the components, sequence of steps, and other variations would be understood to be within the scope of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Example 1. Operation of the ADH, ALDH and NOX System in Solution

Figure 2:
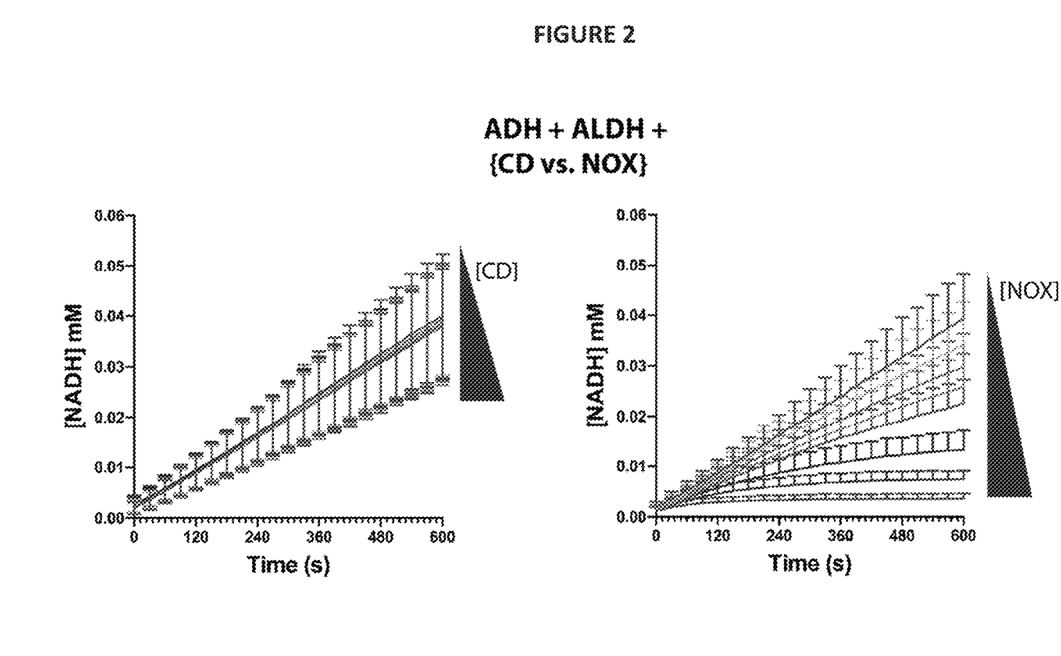
FIG. 2 depicts data demonstrating that increasing amounts of NOX, when combined with ADH and ALDH in vitro, decreases the production of NADH. At the highest amount of NOX, equilibrium is reached with no increased production of NADH.

FIG. 2 shows that combination of ADH, ALDH and NOX in solution produces the desired activity. Each curve in the graph on the right of FIG. 2 represents a different mixture of ADH, ALDH, and NOX. ADH and ALDH are present in a fixed mass ratio of 1:500 in all mixtures. ADH is present at 0.2 ng/ml. The enzyme cytosine deaminase (CD) which has no NADH oxidase activity (left panel) or NOX (right panel) is added to the system at increasing mass concentration as follows (top to bottom): 0.9, 1.8, 2.7, 3.6, 7.2, 14.4, 28.8 ng/ml. Ethanol and NAD+ are initially both present at 10 mM. When NOX is added to the mixture in increasing amounts, the rate of NADH accumulation, measured by spectrophotometry, is seen to decrease. This indicates that NOX actively converts NADH to NAD+ until the rates of NADH generation by ADH and ALDH reach equilibrium with the rate of NADH utilization by NOX. The system with increasing concentrations of CD showed no reduction in NADH concentration. ADH, ALDH, and NOX here were derived from *Saccharomyces cerevisiae* (ADH1), *Homo sapiens* (ALDH2), and *Streptococcus pyogenes* (NOX).

The buffer conditions used were as follows: 50 mM potassium phosphate, pH=8, and 10 mM NAD+. ADH, ALDH, and NOX were derived from *Saccharomyces cerevisiae* (ADH1), *Homo sapiens* (ALDH2), and *Streptococcus pyogenes* (NOX), respectively. NADH was detected by spectroscopy by measuring absorbance at 340 nm.

Example 2. Liposomes Containing ADH, ALDH and NOX Produce Acetate from Ethanol

Figure 3:
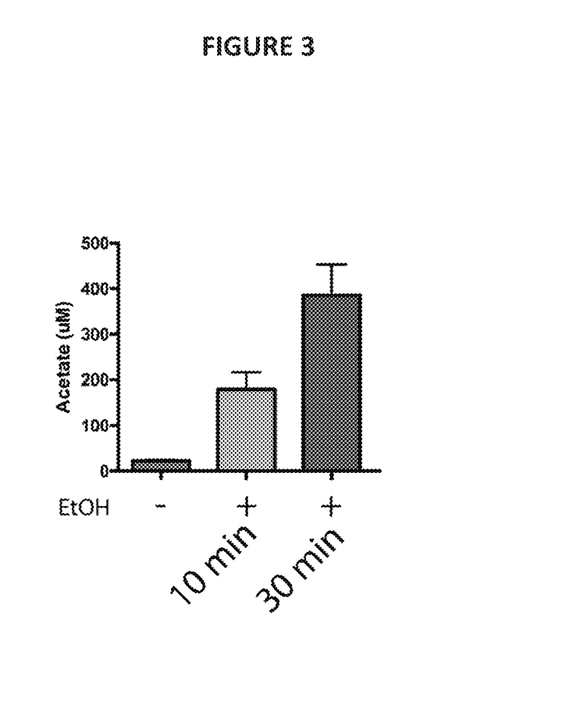
FIG. 3 shows that liposomes containing ADH, ALDH and NOX enzymes produce acetate, only when ethanol is present.

FIG. 3 shows that liposomes containing ADH, ALDH, and NOX enzymes produce acetate from ethanol. Acetate was measured by with a detection kit (Abcam) that enzymatically produces a colorimetric readout detectable by spectroscopy. Liposomes were prepared by the inverted emulsion technique, as is well known in the art. Briefly, an aqueous solution containing the desired enzyme mixture is added to mineral oil containing dissolved phospholipids and cholesterol. This is briefly agitated to form micelles. This mixture is then added on top of an aqueous phase containing reaction buffer (potassium phosphate, pH 8, 10 mM NAD+). This reaction is left to sit for 5 minutes to give micelles time to accumulate at the interface of the aqueous and lipid phases. This solution is then centrifuged for 5 minutes at maximum RPM. The liposomes containing the enzyme mix form a pellet at the bottom of the tube and can be retrieved by pipetting or purified using a size exclusion column.

The liposomes were suspended in a solution either containing no ethanol (blue bar) or ethanol (green bars). Acetate is produced only in the presence of ethanol, indicating that liposomes contain active enzymes. The mass ratio of ADH, ALDH, and NOX in the liposome formulation was 1:500:70, respectively. ADH was present at 0.2 ng/ml.

Example 3. Liposomes Containing ADH, ALDH and NOX Recycle NADH

Figure 4:
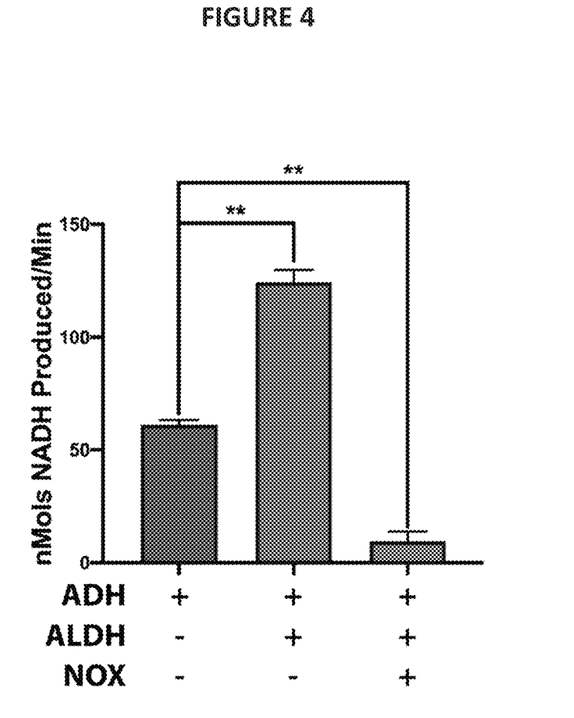
FIG. 4 depicts data demonstrating NOX activity when combined with ADH and ALDH in liposomes. The inclusion of NOX in the liposomes reduces the accumulation of NADH, thereby generating a higher concentration of NAD+ in the liposome.

FIG. 4 shows that NADH production reaches low steady-state levels when liposomes containing NOX, ADH, ALDH, and 10 mM NAD+ are suspended in a solution containing 10 mM ethanol after 30 minutes. Each bar represents the amount of NADH produced by a liposomal formulation of either ADH alone, ADH and ALDH, or all three enzymes. The legend at the bottom shows which enzyme molecules are present in the liposomes (− indicates absence, + indicates presence). Addition of NOX to ADH+ALDH reduces the rate of NADH accumulation, indicating that NOX is active in the liposomal formulation and is generating NAD+.

The buffer conditions inside the liposomes were as follows: 50 mM Potassium phosphate, pH=8, and 10 mM NAD+. Liposome composition was 50% POPC and 50% cholesterol. ADH, ALDH, and NOX here were derived from *Saccharomyces cerevisiae* (ADH1), *Homo sapiens* (ALDH2), and *Streptococcus pyogenes* (NOX). The mass ratio of ADH, ALDH, and NOX in the liposome formulation was 1:500:70, respectively. ADH was present at 0.2 ng/ml.

Figure 5:
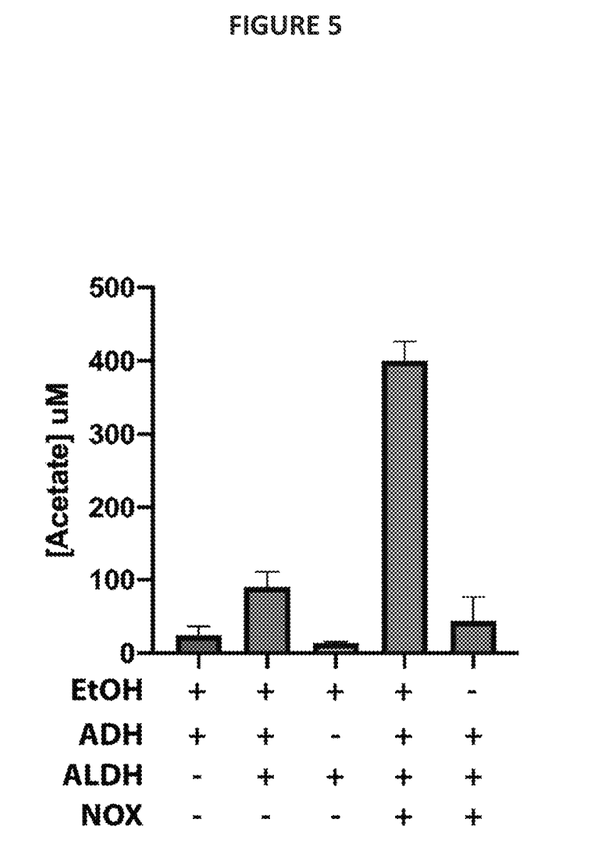
FIG. 5 shows that the inclusion of NOX in liposomes in combination with ADH and ALDH enables greater acetate production from ethanol.

Example 4. Increases Acetate Production from Ethanol by Liposomes Containing NOX FIG. 5 shows that the presence of NOX in liposomes enables greater acetate production. Acetate production is measured from liposomes containing combinations of ADH, ALDH, and NOX. Plus signs (+) indicate the presence and minus signs (−) indicate the absence of the corresponding enzyme or 10 mM ethanol (EtOH), as listed to the left. The presence of NOX in a system containing both ADH and ALDH greatly improves the amount of acetate accumulated, highlighting the essential nature of NOX in the performance of the system.

The buffer conditions inside the liposomes were as follows: 50 mM potassium phosphate, pH=8, and 10 mM NAD+. ADH, ALDH, and NOX were derived from *Saccharomyces cerevisiae* (ADH1), *Homo sapiens* (ALDH2), and *Streptococcus pyogenes* (NOX). Liposome composition was 50% POPC and 50% cholesterol. The mass ratio of ADH, ALDH, and NOX in the liposome formulation was 1:500:70, respectively. ADH was present at 0.2 ng/ml. Acetate was detected as described above.

Example 5. Clinical Use of Ethanol Detoxifying Liposomes

A liposomal formulation comprising ADH, ALDH and NOX is prepared in a phospholipid vesicle approximately 200 nm in diameter. NAD+ is also included inside the liposome. The vesicles are produced by inverted emulsion or microfluidics, followed by extrusion of the liposome through a polymer membrane to achieve the correct size. The microparticles are radiation sterilized and may be lyophilized with cryoprotectant (e.g. fructose, trehalose) for stable storage. Upon presentation of an alcohol poisoning patient in an emergency department, the patient is administered intravenously an amount of rehydrated liposome formulation based on the patient's weight, sex, heart rate, and BAC. Upon injection, the liposome formulation degrades ethanol in the blood of the patient, thereby reducing the toxic effects of alcohol, possibly avoiding fatal complications thereof, and expediting the patient's recovery. Liposomes will over time be eliminated via the liver, spleen, or kidneys. In one embodiment, microparticles are administered by emergency medical personnel before the patient reaches the emergency room.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for continuously removing ethanol from a body cavity or blood of a human subject by converting the ethanol to acetate, the method comprising administering to the subject a composition of liposomes comprising an aqueous phase comprising (i) a system for generating $NAD^+$ from NADH consisting of NADH oxidase (NOX) and oxygen, and (ii) $NAD^+$-dependent enzymes that convert ethanol to acetate, said enzymes consisting of alcohol dehydrogenase (ADH) and acetaldehyde dehydrogenase (ALDH).

2. The method of claim 1, wherein the composition of liposomes is administered to the subject intravenously, intramuscularly, intraperitoneally, or by inhalation.

3. The method of claim 1 wherein the NAD+ dependent ADH is from bacteria, yeast, plants, or mammals.

4. The method of claim 1 wherein the NAD+ dependent ADH is expressed recombinantly.

5. The method of claim 3 wherein the NAD+ dependent ADH is yeast ADH.

6. The method of claim 1 wherein the NAD+ dependent ALDH is from bacteria, yeast, plants, or mammals.

7. The method of claim 1 wherein the NAD+ dependent ALDH is expressed recombinantly.

8. The method of claim 6 wherein the NAD+ dependent ALDH is yeast ADH.

9. The method of claim 1 wherein the NOX is *Streptococcus pyogenes* NOX.

* * * * *